United States Patent
Truschel et al.

(10) Patent No.: US 9,272,111 B2
(45) Date of Patent: Mar. 1, 2016

(54) LEAK ESTIMATION USING FUNCTION ESTIMATION

(75) Inventors: William A. Truschel, Eindhoven (NL); Anandi Mahadevan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 345 days.

(21) Appl. No.: 13/811,781

(22) PCT Filed: Jul. 5, 2011

(86) PCT No.: PCT/IB2011/052973
§ 371 (c)(1),
(2), (4) Date: Jan. 23, 2013

(87) PCT Pub. No.: WO2012/014106
PCT Pub. Date: Feb. 2, 2012

(65) Prior Publication Data
US 2013/0118496 A1    May 16, 2013

Related U.S. Application Data

(60) Provisional application No. 61/368,058, filed on Jul. 27, 2010.

(51) Int. Cl.
*A61M 16/06* (2006.01)
*G06F 17/00* (2006.01)
(Continued)

(52) U.S. Cl.
CPC ............ *A61M 16/06* (2013.01); *A61M 16/0051* (2013.01); *G01F 1/00* (2013.01);
(Continued)

(58) Field of Classification Search
CPC ............ A61M 16/00; A61M 16/0003; A61M 16/0051; A61M 16/0057; A61M 16/0069; A61M 16/06; A61M 16/069–16/0858; A61M 2205/15; A61M 2016/0015; A61M 2016/0027–2016/0042; A61M 2016/102; A61B 5/08; A61B 5/0816; A61B 5/082; A61B 5/083; A61B 5/087; G01F 1/00
USPC ............ 128/200.24, 203.12, 203.14, 204.18, 128/204.21–204.23, 205.11, 205.24, 128/207.14–207.16, 207.18
See application file for complete search history.

(56) References Cited

U.S. PATENT DOCUMENTS 6,402,697 B1 * 6/2002 Calkins ................ A61B 5/0836
600/529
9,028,423 B2 * 5/2015 Bassin ................... A61B 5/085
128/204.23

(Continued)

FOREIGN PATENT DOCUMENTS

| WO | WO9806449 A1 | 2/1998 |
| WO | WO2008025064 A1 | 3/2008 |
| WO | WO2010044038 A2 | 4/2010 |

OTHER PUBLICATIONS

Habre, W., Asztalos, T., Sly, P. D., Petak, F., "Viscosity and density of common anaesthetic gases: implications for flow measurements", 2001, British Journal of Anaesthesia 87(4): 602-7.*

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

The disclosed concept maintains that $Q_p = Q_c - Q_{leak}$, where, $Q_p$ is the estimated patient flow, $Q_{leak}$ is the estimated leak and $Q_c$ is the measured total circuit flow. $Q_{leak}$ is given by a transfer function $\phi(\chi)$ where x is a set of independent measured or fixed variables. The transfer function is thus $Q_{leak} = \phi(\chi)$. The transfer function ($\phi(\chi)$ is adjusted given the constraint that, $Q_p$ shall be zero. The transfer function converges over time to accurately estimate the leak because over an extended time the mean patient flow will always be zero. In one example, $\phi(\chi) = g_{orf} P^\gamma$ and the coefficient $g_{orf}$ is adapted until $Q_p$ is zero.

8 Claims, 2 Drawing Sheets

(51) Int. Cl.
*G01F 1/00* (2006.01)
*A61M 16/00* (2006.01)

(52) U.S. Cl.
CPC .......... *G06F 17/00* (2013.01); *A61M 16/0066* (2013.01); *A61M 2016/0021* (2013.01); *A61M 2016/0039* (2013.01); *A61M 2205/15* (2013.01)

(56) References Cited

U.S. PATENT DOCUMENTS

| | | | | |
|---|---|---|---|---|
| 2002/0023644 A1* | 2/2002 | Berthon-Jones | ....... | A61B 5/085 128/204.22 |
| 2002/0023645 A1* | 2/2002 | Zdrojkowski | ..... | A61M 16/0051 128/204.23 |
| 2003/0171903 A1* | 9/2003 | Rutherford | ........... | G01M 3/007 703/9 |
| 2007/0016093 A1* | 1/2007 | Rapoport | .............. | A61B 5/0002 600/533 |
| 2009/0301486 A1* | 12/2009 | Masic | ........................ | A61B 5/08 128/204.21 |
| 2009/0326403 A1* | 12/2009 | Bassin | .................... | A61B 5/085 600/538 |
| 2010/0236555 A1* | 9/2010 | Jafari | ................. | A61M 16/0051 128/204.23 |
| 2012/0006328 A1* | 1/2012 | Berthon-Jones | ....... | A61B 5/085 128/204.23 |
| 2012/0078542 A1* | 3/2012 | Younes | .............. | A61M 16/0051 702/51 |
| 2013/0110416 A1* | 5/2013 | Hill | .................. | A61M 16/0051 702/46 |
| 2013/0116942 A1* | 5/2013 | Hill | .................. | A61M 16/0051 702/51 |

\* cited by examiner

LEAK ESTIMATION USING FUNCTION ESTIMATION

CROSS-REFERENCE TO RELATED APPLICATIONS

This patent application claims the priority benefit under 35 U.S.C. §371 of international patent application no. PCT/IB2011/052973, filed Jul. 5, 2011, which claims the priority benefit under 35 U.S.C. §119(e) of U.S. Provisional Application No. 61/368,058 filed on Jul. 27, 2010, the contents of which are herein incorporated by reference.

BACKGROUND OF THE INVENTION

1. Field of the Disclosure

The present invention relates to positive gas delivery systems, such as pressure support systems and other ventilator (e.g., invasive) systems, and, more particularly, to a method for estimating leak in a gas delivery system, and a gas delivery system employing such a method.

2. Description of the Related Art

There are numerous situations where it is necessary or desirable to deliver a flow of breathing gas non-invasively to the airway of a patient, i.e., without intubating the patient or surgically inserting a tracheal tube in his or her esophagus. Such therapies are commonly referred to as non-invasive ventilation (NIV) therapies. For example, it is known to non-invasively deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

NIV therapies involve the placement of a patient interface device including a mask component on the face of a patient. The mask component may be, without limitation, a nasal mask that covers the patient's nose, a nasal pillow/cushion having nasal prongs that are received within the patient's nares, a nasal/oral mask that covers the nose and mouth, or a full face mask that covers the patient's face. The patient interface device interfaces the ventilator or pressure support device with the airway of the patient through one or more delivery conduits (together commonly referred to as a patient circuit) so that a flow of breathing gas can be delivered from the pressure/flow generating device to the airway of the patient.

NIV using a single limb patient circuit has safely ventilated patients with respiratory insufficiency for over ten years and those with severe sleep apnea for over twenty years. In NIV, an accurate estimate of the patient flow is required for consistent and accurate volume delivery and for the ventilator to sense the patient's respiratory drive. The accuracy of the estimated patient flow is dependent on two things: (i) the accuracy and precision of the total flow signal (which is measured at the ventilator outlet and which is the composite of the patient flow and the flow caused by leaks (both intentional and unintentional) about the patient interface) and, (ii) the ability to model the leak flow as a function of one or more parameters such as pressure. Thus, one of the key technologies for effective NIV is the estimation of leak flow.

SUMMARY OF THE INVENTION

Furthermore, the ability to accurately estimate leak flow is also important in situations where it is necessary to deliver a flow of breathing gas to the airway of a patient invasively, i.e., wherein the patient is intubated or has a surgically inserted tracheal tube. For example, while mask leak is predominant in NIV, cuff leak is important in invasive circuits. Also, many trached patients have no cuff and therefore the interface is inherently leaky.

Thus, in gas delivery systems such as positive pressure support system and invasive ventilatory system (e.g., that provide volume controlled ventilation), the leak flow that needs to be estimated accurately is defined as any flow escaping the ventilatory system that includes the machine, the patient interface and the patient's trachea and lungs.

The assignee of the invention described elsewhere herein has developed and employed a leak estimation method that is based on the simple principle that a person on a single breath will on average expire the same volume that he or she inspires. This method was based on Bernoulli's orifice flow model, set forth below:

$$Q = C_d A \sqrt{\frac{\Delta P}{\rho}},$$

where Q is the flow through an orifice, $C_d$ is a discharge coefficient (less than 1) based on the principle of vena contracta, A is the cross sectional area of the orifice opening, $\Delta P$ is the pressure differential across the orifice and $\rho$ is the fluid density. This equation was simplified to:

$$Q_{leak} = g_{orf} \sqrt{P_p},$$

where $Q_{leak}$ is the estimated leak flow, $g_{orf}$ is the lumped coefficient that includes area, discharge coefficient and density of the theoretical orifice causing the leak, and $P_p$ is the patient pressure.

In addition, patient flow estimation is governed by the following equation:

$$Q_p = Q_c - Q_{leak},$$

where, $Q_p$ is the estimated patient flow (e.g., computed every 10 milliseconds) and $Q_c$ is the measured total circuit flow.

The current method makes some assumptions. First, it assumes that all leak is located proximal to the patient's applied pressure. Second, it assumes that the discharge coefficient, orifice area and fluid density are all constants throughout the breath. Also, in the current method, $g_{orf}$ is computed on a breath by breath basis with an autoregressive filter according to the following:

$$g_{orf} += \frac{1}{2} \frac{\int_{T_{breath}} Q_p}{\int_{T_{breath}} \sqrt{P_p}}.$$

The original method has been effective without minor deviations in existing gas delivery systems. However, recent trials with trached, pediatric patients have shown that ventilation triggering algorithms employing the existing method at times miss triggers. In addition, recent studies by the assignee of the invention described herein have shown that irregular breathing drives the existing algorithm to compute erroneous leak characteristics. This is due to the fact that inherent in such an algorithm is a conceptual conundrum. More specifically, leak estimation is a key component of breath detection, but, as can be seen from the leak equation, breath detection is a key component of leak estimation. This type of circular dependence is inherently flawed. Therefore if either goes wrong, they both fail.

At least two failure modes should be considered which illustrate problems associated with the current method. In the first, assume a pediatric patient has very low unassisted flow. Triggering algorithms employing the current method may fail to detect breaths due to errors in leak estimation, and because breaths are not detected, leak is never updated to correct the issue. In the second, assume a patient makes a sudden movement and causes a false trigger. The false trigger truncates the leak estimation algorithm and results in erroneous leak estimation. The next trigger will be negatively affected by the wrong leak estimation and the process repeats.

In one embodiment, the invention maintains that $$Q_p = Q_c - Q_{leak},$$

where, $Q_p$ is the estimated patient flow, $Q_{leak}$ is the estimated leak (e.g., estimates may be computed every 10 milliseconds) and $Q_c$ is the measured total circuit flow. $Q_{leak}$ is given by a transfer function $\phi(\chi)$ where x is a set of independent measured or fixed variables. Thus, the transfer function may be expressed as follows:

$$Q_{leak} = \phi(\chi),$$

The invention involves adjusting the transfer function $\phi(\chi)$ given the constraint that, $Q_p$ shall be equal to some value, which in the exemplary embodiment is zero. The transfer function converges over time to accurately estimate the leak because over an extended time the mean patient flow will always be zero.

Thus, in one exemplary embodiment, a method of estimating leak flow $Q_{leak}$ in a gas delivery system is provided that includes determining a patient flow $Q_p$, wherein the patient flow $Q_p$ is a flow of gas delivered to the patient by the gas delivery system, and determining a transfer function $\phi(\chi)$ that estimates the leak flow $Q_{leak}$, where x is a set of independent measured or fixed variables, based on an adaptive filter constraining patient flow $Q_p$.

In another embodiment, a gas delivery system, such as a positive pressure support system (e.g., a CPAP machine) or a ventilator capable of providing volume controlled ventilation invasively or non-invasively, is provided that implements and employs the method of leak estimation just described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
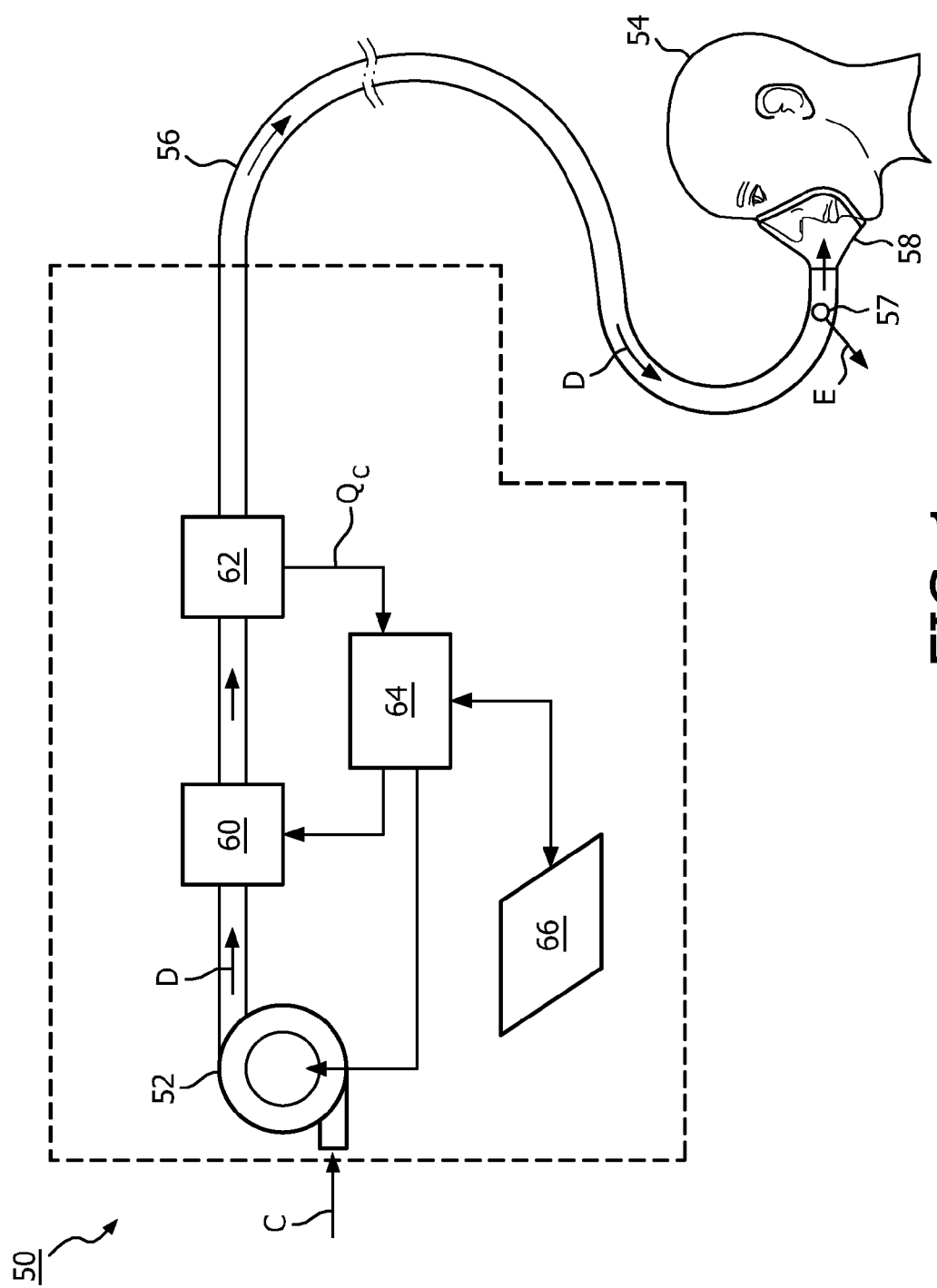
FIG. 1 is a schematic diagram of pressure support system according to one particular, non-limiting embodiment in which the leak estimation methodology of the present invention may be implemented.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As described in greater detail herein, the present invention solves many of the problems of existing leak estimation methods by providing a leak estimation methodology that is a simplified approach to leak estimation and that has no dependence on breath detection. In the exemplary embodiment described elsewhere herein, the methodology still uses the patient pressure power law to maintain the pressure dependence. However, rather than attempting to zero the sum of the estimated patient flow on a breath by breath basis, the methodology of the present invention zeroes the estimated patient flow over an extended period of time.

FIG. 1 is a schematic diagram of pressure support system 50 according to one particular, non-limiting embodiment in which the leak estimation methodology of the present invention may be implemented. It should be understood that pressure support system 50, which is a NIV system, is meant to be exemplary only for purposes of illustrating and describing the present invention, and that the present invention may be implemented and employed in other types of gas delivery systems, such as, without limitation, a ventilator, such as an invasive ventilator system, that delivers volume controlled ventilation. One such alternative gas delivery system is described in PCT Publication No. WO 2010/044038, entitled "Volume Control in a Medical Ventilator," assigned to the assignee of the present invention, the disclosure of which is incorporated herein by reference. The system of WO 2010/044038 provides for invasive ventilation and for leak compensated volume control and delivery with an active circuit (the system includes an active exhalation valve with a proximal flow sensor). Thus, the present invention may be employed in any type of gas delivery system having leaks where it is necessary or desirable to model and compensate for leak flow.

Referring to FIG. 1, pressure support system 50 includes gas flow/pressure generator 52, such as a blower used in a conventional CPAP or bi-level pressure support device, piston, bellows, compressor, or any other device that receives breathing gas, generally indicated by arrow C, from any suitable source, e.g., a pressurized tank of oxygen or air, the ambient atmosphere, or a combination thereof. Gas flow/pressure generator 52 generates a flow of breathing gas, such as air, oxygen, or a mixture thereof, for delivery to an airway of a patient 54 at relatively higher and lower pressures, i.e., generally equal to or above ambient atmospheric pressure.

The pressurized flow of breathing gas, generally indicated by arrow D from gas flow/pressure generator 52 is delivered, via a delivery conduit 56, to breathing mask or patient interface 58 of any known construction, which is typically worn by or otherwise attached to patient 54 to communicate the flow of breathing gas to the airway of the patient. Delivery conduit 56 and patient interface device 58 are typically collectively referred to as a patient circuit.

Although not shown in FIG. 1, the present invention also contemplates providing a secondary flow of gas, either alone or in combination with the primary flow of gas (arrow C) from atmosphere. For example, a flow of oxygen from any suitable source, such as an oxygen concentrator, or oxygen storage device (liquid or gas), can be provided upstream of gas flow/pressure generator 52 or downstream of the gas flow generator, for example, in the patient circuit or at the patient interface device, to control the fraction of inspired oxygen delivered to the patient.

Pressure support system 50 shown in FIG. 1 is a single-limb system, meaning that the patient circuit includes only delivery conduit 56 connecting the patient to the pressure support device. As such, active exhaust valve 57 is provided in the delivery conduit 56 for venting exhaled gasses from the system to atmosphere as indicated by arrow E. It should be noted that the exhaust valve 57 can be provided at other locations in addition to or instead of in the delivery conduit, such as in the patient interface device 58. It should also be understood that exhaust valve 57 can have a wide variety of configurations depending on the desired manner in which gas is to be vented from the pressure support system.

In the illustrated exemplary embodiment of the present invention, patient interface 58 is a nasal/oral mask. It is to be understood, however, that patient interface 58 can include a nasal mask, nasal pillows, tracheal tube, endotracheal tube, or any other device that provides the gas flow communicating function. Also, for purposes of the present invention, the phrase "patient interface" can include delivery conduit 56 and any other structures that connect the source of pressurized breathing gas to the patient.

It is to be understood that various components may be provided in or coupled to the patient circuit. For example, a bacteria filter, pressure control valve, flow control valve, sensor, meter, pressure filter, humidifier and/or heater can be provided in or attached to the patient circuit. Likewise, other components, such as muffler and filters can be provided at the inlet of gas flow/pressure generator 52 and at the outlet of valve 60 (described below).

In the illustrated embodiment, pressure support system 50 includes a pressure controller or flow controller in the form of motor or valve 60 provided in delivery conduit 56. Valve 60 controls the pressure or the flow of breathing gas from gas flow/pressure generator 52 delivered to patient 54. For present purposes, gas flow/pressure generator 52 and valve 60 are collectively referred to as a "pressure generating system" because they act in concert to control the pressure and/or flow of gas delivered to the patient.

It should be apparent that other techniques for controlling the pressure or the flow delivered to the patient by the gas flow/pressure generator, such as varying the blower speed, either alone or in combination with a pressure control valve, are contemplated by the present invention. Thus, valve 60 is optional depending on the technique used to control the pressure of the flow of breathing gas delivered to the patient. If valve 60 is eliminated, the pressure generating system corresponds to gas flow/pressure generator 52 alone, and the pressure of gas in the patient circuit is controlled, for example, by controlling the motor speed of the gas flow/pressure generator.

Pressure support system 50 further includes flow sensor 62 that measures the flow of breathing gas within delivery conduit 56. In accordance with the exemplary embodiment shown in FIG. 1, flow sensor 62 is interposed in line with delivery conduit 56, most preferably downstream of valve 60. Flow sensor 62 generates a flow signal Qc (which, as described elsewhere herein, is the measured total circuit flow) that is provided to controller 64 and is used by controller 64 to determine the flow of gas at the patient Qp. Flow sensor 62 may be included within system, 50, or provided externally as part of delivery conduit 56.

Techniques for calculating $Q_p$ based on $Q_c$ are well known, and take into consideration the pressure drop of the patient circuit, known leaks from the system, i.e., the intentional exhausting of gas from the circuit as indicated by arrow E in FIG. 1, and unknown leaks from the system, such a leaks at the mask/patient interface. As stated elsewhere herein, the present invention provides an improved methodology for calculating leak flow $Q_{leak}$ (which is described in detail below), which may then be used in calculating $Q_p$ based on $Q_c$.

Controller 64 includes a processing portion which may be, for example, a microprocessor, a microcontroller or some other suitable processing device, and a memory portion that may internal to the processing portion or operatively coupled to the processing portion and that provides a storage medium for data and software executable by the processing portion for controlling the operation of pressure support system 50, including estimating leak flow $Q_{leak}$ as described in greater detail herein.

Input/output device 66 is provided for setting various parameters used by the variable positive airway pressure support system, as well as for displaying and outputting information and data to a user, such as a clinician or caregiver. It is to be understood that the present invention contemplates providing input/output terminals so that the operation information and data collected by the pressure support system can be monitored and controlled remotely.

In one exemplary embodiment, the present invention provides an improved methodology for leak estimation by employing a transfer function for determining $Q_{leak}$ wherein $Q_{leak} = \phi(g_{orf}, X_i)$. In the transfer function, $X_i$ is one or more known, measured or estimated patient interface, respiratory or ambient condition parameters, and the transfer function is determined based on an adaptive filter constraining $Q_p$ to 0. As used herein, the term "adaptively filtered" or "adaptive filtering" shall mean any method in which the transfer function of the estimator is adapted based on feedback from the input parameters from sensors and/or user entered parameters and/or known characteristics of the system. In the exemplary embodiment, the patient interface parameters may include the type of mask or endotracheal tube used, the respiratory parameters may include patient respiratory mechanics including muscle effort, and/or lung resistance or compliance, and the ambient parameters may include ambient pressure, temperature, humidity and/or gas composition.

In the exemplary embodiment, the transfer function used for leak estimation is $$Q_{leak} = g_{orf} P_p^\gamma,$$

where γ is the exponent that best approximates the fluid mechanics of leak and $P_p$ is the patient pressure (set and controlled by controller 64). Alternatively, $P_p$ may be measured using a pressure sensor provided as part of pressure support system 50. In the exemplary embodiment, γ is set to an empirically determined suitable value, such as, without limitation, 4/7. Furthermore, in the exemplary embodiment, the adaptation of the parameters in the transfer function is simplified to:

$$g_{orf}+=K_{fg}Q_p,$$

where $K_{fg}$ is a floating $g_{orf}$ gain constant that controls the response time of the leak estimator and $K_{fg} \ll 1$.

Figure 2:
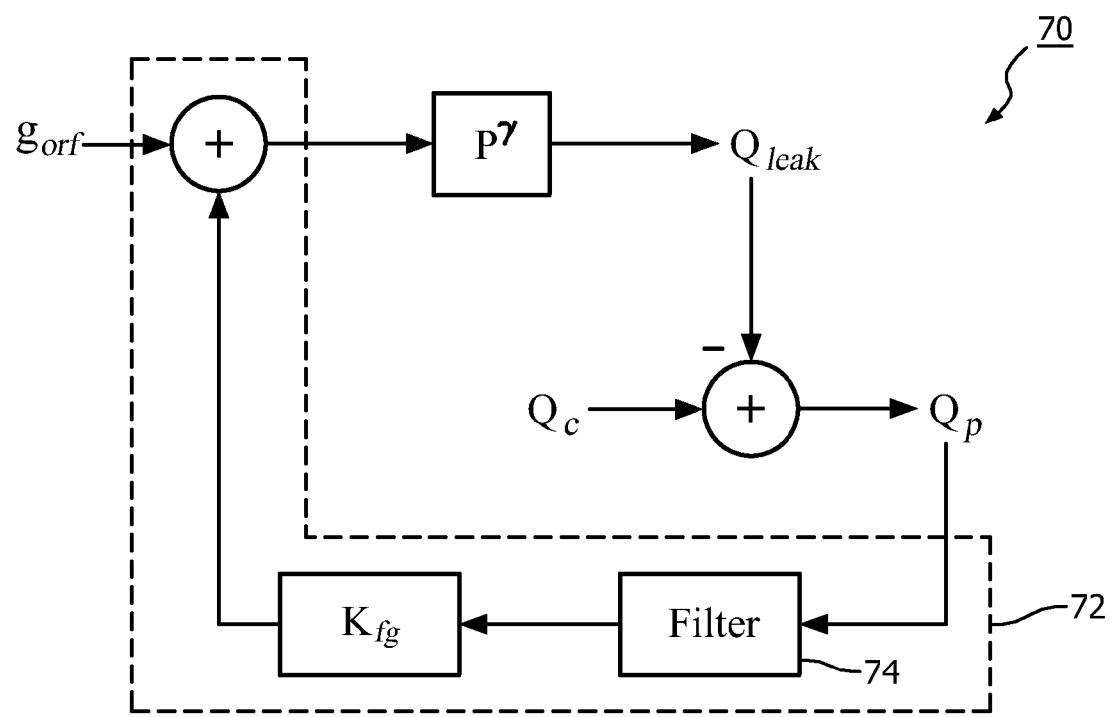
FIG. 2 is a schematic diagram of a transfer function for estimating leak according to an exemplary embodiment of the present invention.

In addition, practice has shown that it is more practical to split up the time constant into two parts. The first part is through a low pass filter for the estimated patient flow $Q_p$ and the second part remains as the gain constant. FIG. 2 is a schematic diagram of the transfer function 70 of the exemplary embodiment of the present invention, wherein the adaptive filter is labeled with reference numeral 72 and includes low pass filter 74, wherein $Q_c$ is measured by flow sensor 62, and wherein $Q_p$ is the estimated patient flow and $Q_{leak}$ is the estimated leak flow. As seen in FIG. 2, the current $g_{orf}$ parameter is obtained by first filtering $Q_p$ and then multiplying the filtered $Q_p$ by $K_{fg}$ and adding the resulting value to the previous $g_{orf}$ parameter. That $g_{orf}$ parameter may then be used to determine the current $Q_{leak}$ based on $Q_{leak}=g_{orf}\cdot P_p^\gamma$.

The floating $g_{orf}$ gain constant $K_{fg}$ is in the exemplary embodiment tuned to provide a near critically damped response of the transfer function after a nominal step changes in leak. A $K_{fg}$ of 1/1230 has been found to be suitable for many cases when the sample rate is 10 msec.

In addition, in the exemplary embodiment, if $g_{orf}$ ever becomes negative ($g_{orf}<0$), which indicates a negative leak, then γ is set equal to zero until $g_{orf}$ becomes positive again. Thus, during the time that $g_{orf}$ is negative the transfer function is adapted to the variant, $Q_{leak}=g_{orf}$. Such a condition may result from oxygen being injected into delivery conduit 56, from a nebulizer being used in conjunction with delivery conduit 56, or from other situations where a gas is being injected into delivery conduit 56.

In the exemplary embodiment, $g_{orf}$ is set equal to zero when therapy using pressure support system 50 is initiated, and the methodology described herein is used to update $g_{orf}$ and determine $Q_{leak}$ periodically, such as, without limitation, every ten milliseconds.

Thus, in short, in the exemplary embodiment just described, the transfer function is given by $Q_{leak}=g_{orf}\cdot P_p^\gamma$, where γ is a predetermined exponent and $P_p$ is patient pressure. In this embodiment, in order to produce zero patient flow, the coefficient $g_{orf}$ is adjusted by filtering the patient flow $Q_p$ to obtain a filtered $Q_p$, multiplying the filtered $Q_p$ by a constant $K_{fg}$ to obtain a product, and adding the product to the previous value of the $g_{orf}$ coefficient.

In another, alternative exemplary embodiment, $Q_{leak}$ or $\phi(\chi)$ is a function of the coefficient $g_{orf}$ and at least one patient interface parameter such as a known leak device inherent to the patient interface. In this embodiment, the transfer function $\phi(\chi)$ may be expressed as follows:

$$Q_{leak}=g_{orf}P_p^\gamma+C_dA\cdot\sqrt{P_p},$$

where A is the known cross-sectional area of a leak device present in the system and $C_d$ is a known discharge coefficient of the orifice.

Furthermore, in this embodiment, the parameters in the transfer function may depend on multiple estimated or measured ambient conditions upon which leak may depend, such as ambient pressure and temperature. In such a case, the transfer function $\phi(\chi)$ may be expressed as follows:

$$Q_{leak}=g_{orf}\cdot P_p^\gamma+C_dA\cdot\sqrt{\frac{P_p}{\rho}},$$

where ρ is the density of the gas delivered as a function of ambient pressure and temperature.

The transfer function may further include known or estimated respiratory parameters such as lung compliance or resistance such as in the case when invasive circuit are used. For example, when the trachea resistance, R, is well known, the transfer function $\phi(\chi)$ may be expressed as follows, which will be a more appropriate model for leak:

$$Q_{leak}=g_{orf}(P_p-RQ_p)^\gamma.$$

Lastly, because it is common that a fixed low flow is often added to the patient circuit, the transfer function may be adapted to include this flow. In such a case, the transfer function $\phi(\chi)$ may be expressed as follows:

$$Q_{leak}=g_{orf}(P_p)^\gamma-Q_{O2}.$$

According to the present invention, that all or some of the parameters in the transfer functions above may be adjusted by method of an adaptive filter using the constraint that patient flow is some predetermined value, which in the exemplary embodiment is zero. In each case, when adapted correctly the leak transfer function will converge to accurately estimate leak over the extended time as the mean patient flow will surely be zero.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method of estimating leak flow $Q_{leak}$ in a gas delivery system, comprising:
   generating a first flow of gas from a pressure or flow generator of the gas delivery system;
   determining a patient flow $Q_p$, wherein the patient flow $Q_p$ is a flow of gas delivered to a patient by the gas delivery system; and
   determining a transfer function $\phi(x)$ that estimates the leak flow $Q_{leak}$, where x is a set of independent measured or fixed variables, based on an adaptive filter constraining patient flow $Q_p$, wherein the constraint regarding patient flow $Q_p$ is patient flow $Q_p$ equals zero, wherein the transfer function $\phi(x)$ is $Q_{leak}=g_{orf}\cdot P_p^\gamma$, where γ is a predetermined exponent, $P_p$ is patient pressure, and $g_{orf}$ is a lumped coefficient, wherein the coefficient $g_{orf}$ is adapted until $Q_p$ is zero, and wherein the determining of the transfer function includes adjusting the coefficient $g_{orf}$ to produce zero patient flow $Q_p$ by filtering the patient flow $Q_p$ to obtain a filtered $Q_p$, multiplying the filtered $Q_p$ by a constant $K_{fg}$ to obtain a product, and adding the product to a previous $g_{orf}$.

2. The method according to claim 1, wherein the filtering of the patient flow $Q_p$ comprises low pass filtering the patient flow $Q_p$.

3. The method according to claim 1, wherein the set of independent measured or fixed variables comprises at least one of a patient interface parameter, a respiratory parameter and an ambient condition parameter.

4. A method of estimating leak flow $Q_{leak}$ in a gas delivery system, comprising:
generating a first flow of gas from a pressure or flow generator of the gas delivery system;
determining a patient flow $Q_p$, wherein the patient flow $Q_p$ is a flow of gas delivered to a patient by the gas delivery system; and
determining a transfer function $\phi(x)$ that estimates the leak flow $Q_{leak}$, where x is a set of independent measured or fixed variables, based on an adaptive filter constraining patient flow $Q_p$, wherein the constraint regarding patient flow $Q_p$ is patient flow $Q_p$ equals zero, wherein the transfer function $\phi(x)$ is $Q_{leak} = g_{orf} \cdot P_p^\gamma$, where $\gamma$ is a predetermined exponent, $P_p$ is patient pressure, and $g_{orf}$ is a lumped coefficient, wherein the coefficient $g_{orf}$ is adapted until $Q_p$ is zero, the method further comprising determining whether $g_{orf}$ is less than 0, and if $g_{orf}$ is less than 0, setting $Q_{leak}$ equal to $g_{orf}$.

5. A gas delivery system, comprising:
a pressure or flow generating system adapted to produce a first flow of gas;
a patient circuit operatively coupled to the pressure or flow generating system; and
a controller operatively coupled to the pressure or flow generating system, the controller being programmed to estimate leak flow $Q_{leak}$ in the gas delivery system by:
determining a patient flow $Q_p$, wherein the patient flow $Q_p$ is a flow of gas delivered to a patient by the gas delivery system; and
determining a transfer function $\phi(x)$ that estimates the leak flow $Q_{leak}$, where x is a set of independent measured or fixed variables, based on an adaptive filter constraining patient flow $Q_p$, wherein the constraint regarding patient flow $Q_p$ is patient flow $Q_p$ equals zero, wherein the transfer function $\phi(x)$ is $Q_{leak} = g_{orf} \cdot P_p^\gamma$, where $\gamma$ is a predetermined exponent, $P_p$ is patient pressure, and $g_{orf}$ is a lumped coefficient, wherein the coefficient $g_{orf}$ is adapted until $Q_p$ is zero, and wherein the determining of the transfer function includes adjusting the coefficient $g_{orf}$ to produce zero patient flow $Q_p$ by filtering the patient flow $Q_p$ to obtain a filtered $Q_p$, multiplying the filtered $Q_p$ by a constant $K_{fg}$ to obtain a product, and adding the product to a previous $g_{orf}$.

6. The gas delivery system according to claim 5, wherein the filtering of the patient flow $Q_p$ comprises low pass filtering the patient flow $Q_p$.

7. The gas delivery system according to claim 5, wherein the set of independent measured or fixed variables comprises at least one of a patient interface parameter, a respiratory parameter and an ambient condition parameter.

8. A gas delivery system, comprising:
a pressure or flow generating system adapted to produce a first flow of gas;
a patient circuit operatively coupled to the pressure or flow generating system; and
a controller operatively coupled to the pressure or flow generating system, the controller being programmed to estimate leak flow $Q_{leak}$ in the gas delivery system by:
determining a patient flow $Q_p$, wherein the patient flow $Q_p$ is a flow of gas delivered to the patient by the gas delivery system; and
determining a transfer function $\phi(x)$ that estimates the leak flow $Q_{leak}$, where x is a set of independent measured or fixed variables, based on an adaptive filter constraining patient flow $Q_p$, wherein the constraint regarding patient flow $Q_p$ is patient flow $Q_p$ equals zero, wherein the transfer function $\phi(x)$ is $Q_{leak} = g_{orf} \cdot P_p^\gamma$, where $\gamma$ is a predetermined exponent, $P_p$ is patient pressure, and $g_{orf}$ is a lumped coefficient, wherein the coefficient $g_{orf}$ is adapted until $Q_p$ is zero, and wherein the controller is further programmed to determine whether $g_{orf}$ is less than 0, and if $g_{orf}$ is less than 0, set $Q_{leak}$ equal to $g_{orf}$.

* * * * *